United States Patent
Wu et al.

(10) Patent No.: US 9,445,592 B2
(45) Date of Patent: *Sep. 20, 2016

(54) COMPLEX FOR USE IN STABILIZING HERBICIDAL COMPOSITIONS AND METHODS FOR SYNTHESIZING AND USING THE SAME

(71) Applicant: BAYER CROPSCIENCE LP, Research Triangle Park, NC (US)

(72) Inventors: Tai-Teh Wu, Chapel Hill, NC (US); Karen L. Eagles, Raymore, MO (US); Michael W. Edenfield, Olathe, KS (US)

(73) Assignee: Bayer CropScience LP, Research Triangle Park, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/106,133

(22) Filed: Dec. 13, 2013

(65) Prior Publication Data

US 2014/0213449 A1    Jul. 31, 2014

Related U.S. Application Data

(60) Division of application No. 12/087,700, filed on Jul. 11, 2008, now Pat. No. 8,642,508, which is a continuation of application No. PCT/US2006/046200, filed on Dec. 4, 2006, which is a continuation-in-part of application No. 11/509,283, filed on Aug. 24, 2006, now Pat. No. 8,883,689, which is a continuation-in-part of application No. 11/295,757, filed on Dec. 6, 2005, now abandoned.

(51) Int. Cl.
*A01N 43/56* (2006.01)
*A01N 43/76* (2006.01)

(52) U.S. Cl.
CPC .................... *A01N 43/56* (2013.01)

(58) Field of Classification Search
None
See application file for complete search history.

(56) References Cited

U.S. PATENT DOCUMENTS

| 6,746,988 | B2 * | 6/2004 | Hopkinson et al. | 504/127 |
| 8,232,231 | B2 | 7/2012 | Huchet et al. | |
| 8,410,025 | B2 | 4/2013 | Huchet et al. | |
| 8,642,508 | B2 * | 2/2014 | Wu et al. | 504/103 |
| 8,716,185 | B2 * | 5/2014 | Huchet et al. | 504/138 |
| 8,883,683 | B2 | 11/2014 | Wu et al. | |
| 8,883,689 | B2 * | 11/2014 | Wu et al. | 504/270 |
| 8,987,169 | B2 | 3/2015 | Huchet et al. | |
| 2002/0042345 | A1 * | 4/2002 | Kocur et al. | 504/211 |
| 2003/0104946 | A1 | 6/2003 | Bickers et al. | |
| 2003/0191026 | A1 | 10/2003 | Killick et al. | |

FOREIGN PATENT DOCUMENTS

| RU | 2260947 | * | 9/2005 |
| RU | 2446685 | * | 4/2012 |
| WO | 98/24321 | | 6/1998 |
| WO | WO 9824321 | * | 6/1998 |

OTHER PUBLICATIONS

Gaillard et al. (FEBS Letters 352,1994,219-221).*
Gaillard et al., FEBS Letters 352, 1994, 219-221.
Nollet et al., Handbook of Water Analysis, CRC Press, Jun. 27, 2000, p. 645.
International Search Report and Written Opinion of PCT/US2006/046200 Dated Nov. 15, 2007.

* cited by examiner

*Primary Examiner* — Alton Pryor

(57) ABSTRACT

The present invention is directed to the discovery, isolation, identification and methods of synthesis of a novel chemical complex that can be used to stabilize mixtures of different chemical compounds, and in particular mixtures of different herbicidal compounds.

9 Claims, 2 Drawing Sheets

COMPLEX FOR USE IN STABILIZING HERBICIDAL COMPOSITIONS AND METHODS FOR SYNTHESIZING AND USING THE SAME

CROSS REFERENCE TO RELATED APPLICATIONS

The application is a Divisional Application of U.S. application Ser. No. 12/087,700, filed Jul. 11, 2008, which is a continuation under 35 USC §111(a) of International Application No. PCT/US2006/046200, which is a continuation-in-part of U.S. application Ser. No. 11/509,283, filed Aug. 24, 2006, which is a continuation-in-part of U.S. application Ser. No. 11/295,757, filed Dec. 6, 2005, the content of all of which are incorporated herein by reference in their entireties.

BACKGROUND OF THE INVENTION

1. Field of the Invention

The present invention relates generally to crop protection compositions and, in one embodiment, to crop protection compositions containing aryloxyphenoxypropionic esters and uses thereof.

2. Description of Related Art

A wide variety of herbicides are in use today. These known herbicides can be effective against different types of undesirable vegetation and can act in different ways. For example, some herbicides are particularly useful when applied to broad leaf plants while others are more useful when applied to grassy plants. Also, these different herbicides can perform their herbicidal function in different ways. For example, some herbicides may act as acetyl-CoA carboxylase inhibitors while others act in a completely different manner, such asacetolactate synthase inhibitors, or carotenoid biosynthesis inhibitors, or mitosis inhibitors, or photosynthesis inhibitors, just to name a few. In order to combat a wide variety of different types of undesirable vegetation, it is not uncommon to combine several different types of herbicides into a single herbicidal composition. This herbicidal composition can then be applied to a field in a single application without having to apply each of the herbicides individually.

An example of one particularly useful group of herbicides are aryloxyphenoxypropionic esters. Aryloxyphenoxypropionic esters typically act as acetyl-CoA carboxylase inhibitors. An example of such herbicides include fenoxaprop esters, such as fenoxaprop ethyl, commercially available from Bayer CropScience, LP. The fenoxaprop esters, such as fenoxaprop ethyl and fenoxaprop p-ethyl, are particularly useful for application to cereal crops to combat grassy weeds. A basic formula for fenoxaprop herbicides is shown in Formula I below.

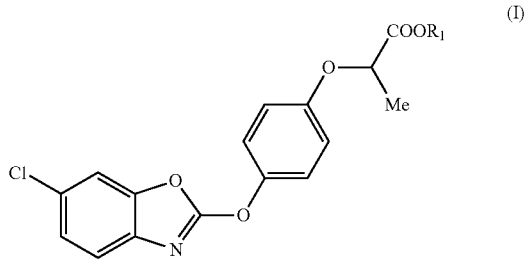

$R_1$ = H: fenoxaprop
$R_1$ = $CH_2CH_3$: fenoxaprop-ethyl
Fenoxaprop p-ethyl

The fenoxaprop ester herbicides are quite well adapted for application to cereal crops and have found widespread acceptance. However, it has been observed that when a fenoxaprop ester herbicide, particularly fenoxaprop ethyl, fenoxaprop p-ethyl or a fenoxaprop lower alkyl ester, is mixed with certain other herbicides, the fenoxaprop ester herbicide can degrade more rapidly than if the fenoxaprop herbicide were not mixed with the other herbicides. This has been particularly observed when a fenoxaprop ester is mixed with herbicides that act as weak acids, such as pyrasulfotole and bromoxynil or bromoxynil mixed esters. This increased degradation of fenoxaprop esters can be disadvantageous to a farmer because it can decrease the useful shelf life of a fenoxaprop ester containing herbicidal composition. And while this phenomenon has been discussed with regard to fenoxaprop ester herbicides to illustrate the problem, the problem is not so limited and can occur with many other mixtures of a variety of herbicides. And, as pointed out above, mixing herbicides is often beneficial, as for example to extend the range of weeds, grasses and the like controlled by the herbicidal mixture or the operative times for control, such as to obtain pre- or post-emergent control of the weeds, grasses and the like at various stages in their life cycle.

Therefore, it would be useful to provide herbicidal compositions that reduce or eliminate the drawbacks associated with previous herbicidal compositions, including but not limited to fenoxaprop ester containing herbicidal compositions.

SUMMARY OF THE INVENTION

The present invention is directed to the discovery, isolation, identification and methods of synthesis of a novel chemical complex that can be used to stabilize mixtures of different chemical compounds, and in particular mixtures of different herbicidal compounds.

The present invention, broadly speaking, may be described in one embodiment as being directed to a novel composition that includes: 1) an acid-sensitive herbicide (by "acid-sensitive" it is meant a herbicide that is negatively affected in an acidic composition), such as fenoxaprop p-ethyl; 2) a weak acid herbicide such as a diketone, triketone, triketonyl oxime herbicide or their keto enol conjugates such as pyrasulfotole; 3) an ester herbicide such as bromoxynil ester; 4) an optional safener such as mefenpyr diethyl; and 5) optionally, a cation donating agent. For example, the cation donating agent may be a substituted aryl sulfonate such as aryl substituted with one or more alkyl or an alkyl sulfonate cation. The alkyl chain length can be from 1 to 30, or 8 to 24, such as 10 to 16, or the mixture of them, such as dodecylbenzenesulfonate calcium, a metal hydride such as calcium hydride, an inorganic salt such as NaCl, $MgCl_2$, $CaCl_2$, or $CaSO_4$, or a moiety that functions in the manner of a cation donating agent such as a protonated primary, secondary, tertiary amine or a quaternary amine, as well as combinations thereof. Examples of diketones, triketones, triketone oxime herbicides and/or their enol conjugates or their masked form include pyrasulfotole, isoxaflutole, clethodim and sethoxydim.

Because the present invention renders the acid sensitive herbicide less susceptible or less negatively impacted by acidic compositions, the composition of the present invention may in fact be co-formulated with an acidic herbicidally active ingredient such as (4-chloro-2-methylphenoxy)-acetic acid (also known as mecaphar or MCPA), 2-(4-chloro-2-methylphenoxy)-propanoic acid (also known as mecoprop or MCPP), 4-(4-chloro-2-methylphenoxy)-butanoic acid (also known as MCPB), 2,4-D, dicamba and other ester herbicides or combinations thereof.

In one embodiment, the novel complex of the present invention stabilizes a herbicidal composition that has been buffered with a buffer system, where the buffer system includes an amine-containing compound capable of forming a complex, and also preferably capable of hydrogen bonding. In a particularly preferred embodiment, the amine-containing compound is an alkyl amine in which one or more of the alkyl components includes a moiety capable of hydrogen bonding, such as an hydroxyl group or an amino group.

In one embodiment, the herbicidal composition in which the novel complex of the present invention is formed is in a herbicidal composition comprising: 1) the grassy weeds herbicide fenoxaprop ethyl or fenoxaprop p-ethyl; 2) the broad leaf weeds herbicide bromoxynil mixed ester; 3) the broad leaf weeds herbicide pyrasulfotole; 4) optionally the safener mefenpyr or mefenpyr diethyl; 5) the amine-containing hydrogen bonding buffer triethanolamine; and 6) optionally, a cation donating agent such as those mentioned above, for example, dodecylbenzenesulfonate calcium.

The present invention is also directed to a method for synthesizing the complex of the present invention comprising the steps of mixing pyrasulfotole, triethanolamine, dodecylbenzene sulfonate calcium in suitable stoichiometric amount in a suitable solvent, preferably an aromatic solvent such as toluene, benzene, xylene, propylene carbonate, Aromatic 100, Aromatic 150, Aromatic 200, the latter three being available from Exxon Mobile Corporation, or combinations thereof, at a suitable temperature range from about −20° C. to about 250° C.

The present invention is also directed to a method for using the novel complex of the present invention to produce a stabilized herbicidal composition which includes two or more herbicidal compounds such as bromoxynil mixed ester and pyrasulfotole and a safener such as mefenpyr diethyl along with suitable surfactant such as a wetting agent, such as dodecylbenzenesulfonate calcium.

DESCRIPTION OF THE PREFERRED EMBODIMENTS

Figure 1:
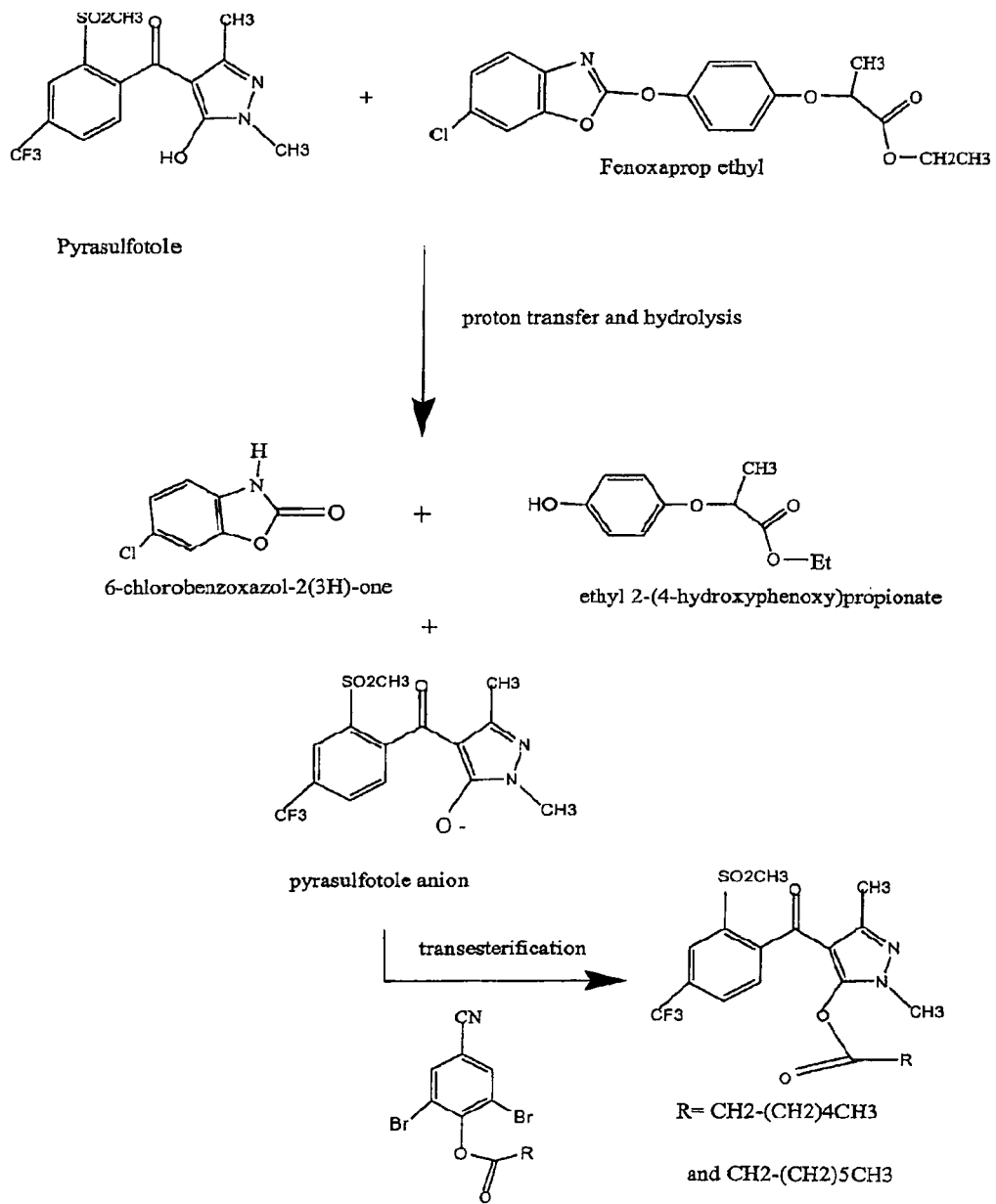
FIG. 1 is a schematic representation of the degradation pathway of a herbicidal composition comprising pyrasulfotole, fenoxaprop p-ethyl, and bromoxynil (mixed esters) illustrating the acid catalyzed hydrolysis of fenoxaprop p-ethyl and the transesterification of pyrasulfotole by virtue of the presence of bromoxynil (mixed esters).

As used herein, all numbers, such as but not limited to dimensions, physical characteristics, processing parameters, quantities of ingredients, reaction conditions, and the like, used in the specification and claims are to be understood as being modified in all instances by the term "about". Accordingly, unless indicated to the contrary, the numerical values set forth in the following specification and claims may vary depending upon the desired properties sought to be obtained by the present invention. At the very least, and not as an attempt to limit the application of the doctrine of equivalents to the scope of the claims, each numerical value should at least be construed in light of the number of reported significant digits and by applying ordinary rounding techniques. Moreover, all ranges disclosed herein are to be understood to encompass the beginning and ending range values and any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more and ending with a maximum value of 10 or less, e.g., 1 to 3.5, 5.5 to 10, 2.3 to 7.3, etc. All references and publications referred to herein, such as but not limited to U.S. patents and published applications, are to be understood as being herein incorporated by reference in their entirety.

As used herein, unless otherwise clear from the context, the term fenoxaprop p-ethyl is used for discussion purposes only and refers to the optical isomer of fenoxaprop, but all forms of fenoxaprop in acid, salts of its acid or ester form are contemplated as within the scope of the present invention.

Similarly, as used herein unless otherwise clear from the context, the term mefenpyr diethyl is used for discussion, but all forms of its esters, acids and salts of its acids, including but not limited to methyl and ethyl esters are contemplated as within the scope of the present invention.

Also, as used herein, unless otherwise clear from the context, the term bromoxynil mixed ester is used for discussion, but all forms of bromoxynil, including single and mixed esters and free phenols, and oxides with various cations (metal or non-metal) are contemplated as within the scope of the present invention.

In one non-limiting embodiment, a herbicidal composition of the invention comprises a aryloxyphenoxypropionic ester, such as a fenoxaprop ester herbicide (optically active or racemic mixture), a buffer system, optionally one or more weak acid herbicides, optionally one or more safeners and optionally a cation donating agent.

Aryloxyphenoxypropionic esters have been described above. Non-limiting examples of aryloxyphenoxypropionic esters are described, for example, in U.S. Pat. Nos. 6,908,883 B2 and 6,887,827 B2. The present invention will be described with respect to the use of a fenoxaprop ester, such as fenoxaprop ethyl or fenoxaprop p-ethyl, in a herbicide composition. However, it is to be understood that the invention is not limited to use with fenoxaprop ethyl or fenoxaprop p-ethyl but is believed to be applicable to other herbicidal compounds including other aryloxyphenoxypropionic esters, e.g., fenoxaprop esters.

The buffer system of the present invention must be capable of forming a complex, preferably additionally with hydrogen bonding, but can be a weak acid buffer system and can comprise a water-miscible acid and a water-miscible salt of the acid. In a highly advantageous embodiment of the invention, the water-miscible acid is a herbicide. By the term "weak acid" is meant an acid with a $pK_a$ in the range of 0.1 to 10 at 25° C. The buffer system is configured to maintain the pH of the herbicidal composition in the range of 4 to 10, e.g., 4 to 8, e.g., 4.5 to 8, e.g., 5 to 7.5, e.g., 5.8 to 7.5. For example, the buffer system could maintain the pH of the herbicide composition in the range of 4 to 7, such as 5 to 7, such as 5 to 6.

The salt of the weak acid can be an amine or imine salt of the weak acid. Substantially non-nucleophilic conjugate amines are preferred to prepare the amine salts. Tertiary alkyl amines are most preferred, although secondary alkyl amines and primary alkyl amines may be used. The amine can also comprise primary, secondary, and/or tertiary amine function in any combination within the same molecule or the mixture of them. For example, the amine can be a tertiary amine such as a trialkylamine in which the alkyl can be optionally substituted with a hydroxy group or an amino group to provide the hydrogen bonding.

Generally one or more of the alkyl moieties of the amine has from 1 to 50 carbons, preferably from 1 to 10 carbons, and, in an alternative embodiment, has from 2 to 6 carbons. The alkyl group can be straight chained, branched, or cyclic alkyl. The one or more alkyl moieties can be, independent of one another, optionally substituted by one or more groups capable of hydrogen bonding such as ether groups, e.g. alkoxy, hydroxyl groups, thiol groups, alkylthio, hydroxysulfonyl, amino sulfonyl, alkylaminosulfonyl, aminosulfenyl, alkylaminosulfenyl, amino sulfinyl, alkylaminosulfinyl, amino, alkylamino, dialkylamino, hydroxysulfonyl, hydroxysufenyl, hydroxysulfinyl, hydroxycarbonyl, or combinations of these functional groups that include a carbon to carbon double bond (i.e., an alkene) or carbon to carbon triple bond (i.e., an alkyne). The amine can be in the form of monoamine or diamine or polyamine. In a preferred embodiment, the one or more alkyl moieties of the amine may be hydroxylated, ethoxylated, diethoxylated, triethoxylated, or substituted with hydroxyethoxy or hydroxypropoxy groups wherein the number of ethoxy and propoxy groups may be from 1 to 60, provided they are capable of hydrogen bonding and/or forming a complex and/or forming a coordination compound.

It is particularly desirable for the present invention that the amine is capable of forming a complex, and is also preferably capable of hydrogen bonding intramolecularly or intermolecularly in order to contribute to the formation of the complex of the present invention as described in more detail herein. In that regard, trialkyl amines with at least one alkyl group substituted with a moiety capable of forming a complex and also preferably capable of hydrogen bonding is preferred. Particularly preferred are alkyl groups substituted with one or more hydroxyl groups, and trialkyl amines wherein each of the alkyl groups has been substituted with an hydroxyl group are particularly preferred. Particularly preferred is triethanolamine.

The herbicidal composition that is stabilized by the complex of the present invention can be in any formulation form including liquid and solid, particularly a liquid composition, such as an emulsifiable concentrate, suspoemulsion, suspension concentrate, or a solution, such as an aqueous solution or an oil solution. In one non-limiting embodiment, an emulsifiable concentrate and a suspoemulsion is preferred.

The conjugate base of the amine salt may also serve as a surfactant in the composition, such as a nonionic surfactant or an ionic surfactant.

Representative conjugate amines and imines include one or more of the following: tertiary amines such as triethanolamine, triisopropanolamine; trialkylamines such as ethyldiethanolamine, N,N,N'',N''-tetrakis-(2-hydroxypropyl) ethylene diamine, tallowalkyl-dimethylamine, ethoxylated alkylamines such as ethoxylated(n) cocoalkylamine, ethoxylated (n) tallowalkylamine, ethoxylated (n) soyaalkylamine, ethoxylated cottonseed amine, oleyl amine ethoxylate, ethoxylated(n) octadecylamine, (ethoxy group numbers n may be from 1 to 60), ethoxylated diamines, such as ethoxylated(n) N-tallow-1,3-diamineopropane, ethoxylated (n) N-tallow-1,3-diaminopropane, ethoxylated(n) N-tallow-1,3-diaminopropane,N,N-bis[α-ethyl-ω-hydroxypoly(oxyethylene)-alkylamine; the poly(oxyethylene) content average 3 moles; the alkyl groups (C14-C18) are derived from tallow, or from soybean or cottonseed oil acids, or other crop or vegetable seeds oil acids. N,N-bis(2-hydroxyethyl)alkylamine, where the alkyl groups (C8-C18) are derived from coconut, cottonseed, soya, or tallow acids or other crops or vegetable seed acids; N,N-Bis 2-(ω-hydroxypolyoxyethylene)ethyl)alkylamine; the reaction product of 1 mole N,N-bis(2-hydroxyethyl)alkylamine and 3-60 moles of ethylene oxide, where the alkylgroup (C8-C18) is derived from coconut, cottonseed, soya, or tallow acids or other crop or vegetable seed acids. N,N-Bis-2-(ω-hydroxypolyoxyethylene/polyoxypropylene)ethyl alkylamine; the reaction product of 1 mole of N,N-bis(2-hydroxyethyl alkylamine) and 3-60 moles of ethylene oxide and propylene oxide, where the alkyl group (C8-C18) is derived from coconut, cottonseed, soya, or tallow acids or other crop seeds or vegetable seeds acids, N,N'-Bis,(2-hydroxyethyl)-C12-C18 alkylamine, N,N'-bis(polyoxyethylene)cetylamine, N,N'-Bis (polyoxyethylene)oleylamine, N,N'-bis(polyoxyethylene) stearyl amine, N,N'-dinitropentamethylenetetramine, ethoxylated abietylamine. Secondary amine such as ethylethanolamine. Primary amine such as ethanolamine, isopropanolamine, polyoxyethylated primary amine (C14-C18); the fatty amine is derived from an animal source and contains 3% water, the poly(oxyethylene) content average 20 moles, amines, C14-C15 alkyl, ethoxylated, amines, C16-C18 and C18 unsaturated, alkyl, ethoxylated amines, tallowalkyl, ethoxylated with polyethylene, triethylene tetramine, ethylendiamine, diethyleneamine, diethylenetriamine, N-oleyl-1,3-propanediamine, tetramethylene pentamine, polypropylene glycol bis(2-aminopropyl)ether, 2-[(2-aminoethyl)amino]ethanol, 2-amino-2-methyl-1-propanol. Imines such as N,N'-disalicylidene-1,2-diaminopropane are included within the scope of the present invention.

The herbicidal compositions that can be stabilized with the complex of the present invention also can include one or more weak acids. In fact, as explained in more detail below, the complex of the present invention is particularly effective for certain combinations of herbicides where the interaction of the herbicides themselves leads to the undesired instability of the herbicidal composition. For example, where the herbicidal composition includes pyrasulfotole and bromoxynil mixed ester in the absence of the buffer system of the present invention, as explained in more detail below, the bromoxynil or bromoxynil mixed esters induces an undesirable transesterification of the pyrasulfotole which causes the degradation of the pyrasulfotole and the degradation of bromoxynil mixed esters. Formation of the complex of the present invention protects the pyrasulfotole and bromoxynil mixed esters from such transesterification and degradation and degradation of bromoxynil mixed ester through hydrolysis of bromoxynil mixed esters despite the presence of bromoxynil mixed esters. Non-limiting examples of representative weak acids included within the scope of the present invention include the following: phenols, phenol esters and mixtures of phenols and phenol esters, substituted phenols, conjugated diketones, conjugated triketones, carboxylic acids or their esters or their salts, such as alkylcarboxylic acids, aryloxycaboxylic acids, phenylcarboxylic acids, phenoxy acetic acids, phenoxy propionic acids and their substituted on the ring and branched analogs and ester analogs.

Non-limiting examples of representative weak acids that are agriculturally acceptable herbicides include the following: pyrazole herbicides such as pyrasulfotole, nitrile herbicides such as bromoxynil, chloroxynil, or ioxynil, or a propesticidal precursor thereof, for example, bromoxynil octanoate or bromoxynil heptanoate, 2,4-D, Dicamba, MCPA, MCPP, or MCPB and their salts with various counter ions and their various esters The herbicide composition may also include an agriculturally acceptable safener, such as but not limited to mefenpyr, mefenpyr diethyl, isoxadifen, fenchlorazole, cloquintocet or combinations thereof, just to name a few.

The inventors have found that the novel complex of the present invention is not always a factor in the stabilization of herbicidal compositions. Where the novel complex is not contributing to the stability of the herbicidal composition it is postulated that either the novel complex of the present invention does not form, or if formed, it does not necessarily contribute to the stability of the herbicidal composition. To appreciate the novel complex of the present invention, it may be helpful to first understand at least in one instance when it is and when it is not necessary to prevent degradation of the herbicidal composition.

The inventors have found that where a herbicidal composition comprises (by weight percent based on the total weight of the composition) 3 wt. % to 6 wt. % pyrasulfotole, 7 wt. % to 10 wt. % fenoxaprop-ethyl, 0.01 wt. % to 4 wt. % of an amine containing buffer, and, optionally, 3 wt. % to 6 wt. % mefenpyr diethyl, such a composition stabilizes in the presence of a buffer system, whether or not the amine-containing buffer system is also capable of hydrogen bonding or forming the complex of the present invention. The remainder of the composition can comprise fillers as are conventional in the art. The components can be emulsified and/or can be dissolved or dispersed in any conventional solvent. But as illustrated in Comparative Examples 1 through 3 below, the mere presence of the amine-containing buffer system (Comparative Examples 1 and 3, (where amine-containing buffer of Comparative Example 1 is capable of hydrogen bonding while the amine-containing buffer of Comparative Example 3 is not) contributed to the stability of that particular herbicidal composition over the herbicidal composition of Comparative Example 2 which did not include such an amine-containing buffer system. In the following Tables, the percentages relating to the proportions of the ingredients in the respective compositions are given in weight percent of the total weight of the respective composition. Due to rounding of figures, all weight percent totals may not be exactly 100%.

Comparative Example 1

An emulsifiable concentrate of fenoxaprop-ethyl, mefenpyr diethyl, and pyrasulfotole and fillers was prepared. Triethanolamine, a buffer capable of hydrogen bonding, was selected as the buffer. The mixture of Table 1 was prepared by mixing the liquid ingredients, then the solid ingredients at 50° C.

TABLE 1

| INGREDIENTS |
| --- |
| Pyrasulfotole (99% pure), 4.85% |
| Mefenpyr diethyl (94.8% pure), 3.64% |
| Fenoxyprop p-ethyl (94% pure), 8.92% |
| [1]Alkyl alcohol ethoxylate, 6.00% |
| Castor oil ethoxylated, 6.00% |
| [2]Benzene sulfonic acid, calcium salt, 10.00% |
| Propylene carbonate, 15.00% |
| Triethanolamine, 2.70% |

TABLE 1-continued

| INGREDIENTS |
| --- |
| [3]Aromatic organic solvent, 42.89% |

[1]Containing on the average an aliphatic chain of 11 to 15 carbons and ethoxylated to an average of 4 to 8 moles
[2]In this Table and the following Tables, benzene sulfonic acid calcium salt is the same as dodecylbenzene sulfonate calcium (DBSCa)
[3]A150 commercially available from Exxon Corporation The mixture was tested for long-term storage stability by subjecting separate samples to different temperatures for eight weeks. The following test results were obtained and are shown in Table 2.

TABLE 2

| | Avg. Wt % | Avg. Wt % | Avg. Wt % |
| --- | --- | --- | --- |
| | Active ingredient name | | |
| | Pyrasulfotole | Mefenpyr Diethyl | Fenoxaprop p-ethyl |
| 8 weeks @ 0° C. | 5.57 | 3.77 | 9.41 |
| 8 weeks @ room temp. | 5.67 | 3.76 | 9.34 |
| change from 0° C. | 1.71% | −0.17% | −0.69% |
| 8 weeks @ 40° C. | 5.53 | 3.74 | 9.00 |
| change from 0° C. | −0.82% | −0.65% | −4.31% |
| 8 weeks @ 50° C. | 5.51 | 3.72 | 8.58 |
| change from 0° C. | −1.12% | −1.17% | −8.83% |

Comparative Example 2

A mixture of fenoxaprop p-ethyl, mefenpyr diethyl, pyrasulfotole, and fillers was prepared in similar manner as in Table 1 but without a buffer system of the invention (see Table 3).

TABLE 3

| INGREDIENTS |
| --- |
| Pyrasulfotole (99% pure), 4.85% |
| Mefenpyr diethyl (94.8% pure), 3.64% |
| Fenoxyprop p-ethyl (94% pure), 8.92% |
| [1]Alkyl alcohol ethoxylate, 6.00% |
| Benzene sulfonic acid calcium salt, 6.00% |
| Epoxidized soy oil, 2.00% |
| [2]Ethoxylated sulfate, 8.00% |
| Propylene carbonate, 15.00% |
| [3]Aromatic organic solvent, 45.59% |

[1]Containing on the average an aliphatic chain of 11 to 15 carbons and ethoxylated to an average of 4 to 8 moles
[2]Ammonium salt of tristyrylphenol that includes 12 to 20 moles of ethylene oxide
[3]A150 commercially available from Exxon Corporation.

The mixture was tested for long-term storage stability by subjecting separate samples to different temperatures for eight weeks. The following test results were obtained and shown in Table 4.

TABLE 4

| | Avg. Wt % | Avg. Wt % | Avg. Wt % |
| --- | --- | --- | --- |
| | Active ingredient name | | |
| | Pyrasulfotole | Mefenpyr diethyl | Fenoxaprop p-ethyl |
| 8 weeks @ 0° C. | 4.76 | 3.81 | 8.20 |
| 8 weeks @ room temp. | 4.75 | 4.01 | 6.49 |
| change from 0° C. | −0.21% | +5.24% | −20.85% |
| 8 weeks @ 40° C. | 4.69 | 3.85 | 2.64 |
| change from 0° C. | −1.47% | −1.05% | −67.80% |

TABLE 4-continued

| | Avg. Wt % | Avg. Wt % | Avg. Wt % |
|---|---|---|---|
| | | Active ingredient name | |
| | Pyrasulfotole | Mefenpyr diethyl | Fenoxaprop p-ethyl |
| 8 weeks @ 50° C. | 4.54 | 3.97 | 0.91 |
| change from 0° C. | −4.62% | −4.20% | −88.90% |

Comparative Example 3

An emulsifiable concentrate of fenoxaprop p-ethyl, mefenpyr diethyl, and pyrasulfotole was prepared. Triethylamine, a buffer that is not capable of complexing or forming a coordination complex or hydrogen bonding, was selected as the buffer. The mixture of Table 5 was prepared by mixing the liquid ingredients, then the solid ingredients at 50° C.

TABLE 5

| INGREDIENTS |
|---|
| Pyrasulfotole (99% pure), 4.85% |
| Mefenpyr diethyl (94.8% pure), 3.64% |
| Fenoxyprop p-ethyl (94% pure) 8.92% |
| [1]Alkyl alcohol ethoxylate, 6% |
| Castor oil ethoxylated, 6% |
| Benzene sulfonic acid, calcium salt 10% |
| Propylene carbonate, 15% |
| Triethylamine, 1.5% |

[2]Aromatic organic solvent, 44.09%
[1]Containing on the average an aliphatic chain of 11 to 15 carbons and ethoxylated to an average of 4 to 8 moles
[2]A150 commercially available from Exxon Corporation The mixture was tested for long-term storage stability by subjecting separate samples to different temperatures for eight weeks. The following test results were obtained and are shown in Table 6.

TABLE 6

| | Avg. Wt % | Avg. Wt % | Avg. Wt % |
|---|---|---|---|
| | | Active ingredient name | |
| | Pyrasulfotole | Mefenpyr diethyl | Fenoxaprop p-ethyl |
| 8 weeks @ 0° C. | 5.38 | 3.80 | 2.93 |
| 8 weeks @ room temp. | 5.46 | 3.77 | 2.89 |
| change from 0° C. | 1.51% | −0.87% | −1.19% |
| 8 weeks @ 40° C. | 5.43 | 3.72 | 2.80 |
| change from 0° C. | 0.85% | −2.10% | −4.37% |
| 8 weeks @ 50° C. | 5.60 | 3.73 | 2.74 |
| change from 0° C. | 4.07% | −1.93% | −6.39% |

As may be seen from the foregoing, where the herbicidal composition does not introduce the special problem of transesterification of the pyrasulfotole as discussed in more detail below, the amine-containing buffer system—whether capable of hydrogen bonding or not—operates to stabilize the composition in comparison to a composition that does not include the buffer system.

One might have expected that with the mere addition of yet another herbicide the pattern would continue. However, the inventors have found that if certain additional herbicides are introduced into the herbicidal composition, such as for example bromoxynil mixed esters, only the buffering systems that are capable of forming complexes, coordination compounds or hydrogen bonding (e.g. triethanolamine containing buffer system) provides the desired stability. The inventors have found that where a herbicidal composition comprises (by weight percent based on the total weight of the composition) 0.5 wt. % to 8 wt. % pyrasulfotole, 1 wt. % to 15 wt. % fenoxaprop p-ethyl, 1 wt. % to 30 wt. % bromoxynil, bromoxynil mixed ester 0.1 wt. % to 10 wt. % and preferably 1 wt. % to 3 wt. % of an amine containing buffer, and, optionally, 0.5 wt. % to 10 wt. % mefenpyr diethyl, such a composition stabilizes only in the presence of a buffer system capable of forming a complex as illustrated in Example 1 and Comparative Example 4 below. The remainder of the composition can comprise fillers as are conventional in the art. The components can be emulsified and/or can be dissolved or dispersed in any conventional solvent.

Example 4

An emulsifiable concentrate of fenoxaprop p-ethyl, mefenpyr diethyl, pyrasulfotole, and bromoxynil mixed esters was prepared. Triethanolamine, a buffer capable of complexing was selected as the buffer. The mixture of Table 7 was prepared by mixing the liquid ingredients, then the solid ingredients at 50° C.

TABLE 7

| INGREDIENTS |
|---|
| Pyrasulfotole (99% pure), 1.4% |
| Bromoxynil mixed esters, 12.86% |
| Mefenpyr diethyl (94.8% pure), 1.84% |
| Fenoxyprop p-ethyl (94% pure), 4.04% |
| [1]Alkyl alcohol ethoxylate, 20% |
| Castor oil ethoxylated, 2% |
| Benzene sulfonic acid, calcium salt 4% |
| Triethanolamine, 0.70% |
| N,N-dimethyldecanamide, 15% |
| [2]Aromatic organic solvent, 35.16% |
| Etho-propoxylated tristyrylphenol, 2% |
| 2-ethyl hexanol, 1% |

[1]Containing on the average an aliphatic chain of 11 to 15 carbons and ethoxylated to an average of 4 to 8 moles
[2]A200 commercially available from Exxon Corporation The mixture was tested for long-term storage stability by subjecting separate samples to different temperatures for eight weeks. The following test results were obtained and are shown in Table 8.

TABLE 8

| | Avg. Wt % | Avg. Wt % | Avg. Wt % | Avg. Wt % |
|---|---|---|---|---|
| | | | Active ingredient | |
| name | Pyrasulfotole | Mefenpyr diethyl | Bromoxynil Mixed Esters | Fenoxaprop p-ethyl |
| 8 weeks @ 0° C. | 1.42 | 1.82 | 7.93 | 4.32 |
| 8 weeks @ room temp. change from 0° C. | | | | |
| 8 weeks @ 40° C. | 1.40 | 1.80 | 7.85 | 3.96 |

TABLE 8-continued

| name | Avg. Wt % Pyrasulfotole | Avg. Wt % Active ingredient Mefenpyr diethyl | Avg. Wt % Bromoxynil Mixed Esters | Avg. Wt % Fenoxaprop p-ethyl |
|---|---|---|---|---|
| change from 0° C. | −1.30% | −0.92% | −1.01% | −8.25% |
| 8 weeks @ 50° C. change from 0° C. | | | | |

Comparative Example 5

An emulsifiable concentrate of fenoxaprop p-ethyl, mefenpyr diethyl, pyrasulfotole and bromoxynil mixed esters was prepared. Triethylamine, a buffer that is not capable of complexing was selected as the buffer. The mixture of Table 9 was prepared by mixing the liquid ingredients, then the solid ingredients at 50° C.

TABLE 9

INGREDIENTS

Pyrasulfotole (99% pure), 1.40%
Bromoxynil mixed esters, 12.86%
Mefenpyr diethyl (94.8% pure), 1.84%
Fenoxyprop p-ethyl (94% pure) 4.040%
[1]Alkyl alcohol ethoxylate, 20%
Castor oil ethoxylated, 2%
Propylene carbonate, 15%
Triethylamine, 0.80%
[2]Aromatic organic solvent, 39.06%
2-ethylhexanol, 1%
Etho-propoxylated tristyrylphenol, 2%

[1]Containing on the average an aliphatic chain of 11 to 15 carbons and ethoxylated to an average of 4 to 8 moles
[2]A150 commercially available from Exxon Corporation The mixture was tested for long-term storage stability by subjecting separate samples to different temperatures for eight weeks. The following test results were obtained and are shown in Table 10.

TABLE 10

| name | Avg. Wt % Pyrasulfotole | Avg. Wt % Active ingredient Mefenpyr diethyl | Avg. Wt % Bromoxynil Octanoate | Avg. Wt % Fenoxaprop p-ethyl |
|---|---|---|---|---|
| 8 weeks @ 0° C. | 1.38 | 1.73 | 5.67 | 4.30 |
| 8 weeks @ room temp. | 1.30 | 1.75 | 5.65 | 4.33 |
| change from 0° C. | −5.80% | 0.77% | −0.41% | 0.07% |
| 8 weeks @ 40° C. | 1.26 | 1.75 | 5.02 | 4.33 |
| change from 0° C. | −9.04% | 0.88% | −11.52% | 0.68% |
| 8 weeks @ 50° C. change from 0° C. | | | | |

As may be seen, in Table 8 there is a much smaller loss of pyrasulfotole (−1.30% at 8 weeks) in the triethanolamine-containing composition over that of Table 10 (−9.04% at 8 weeks) of the triethylamine-containing composition, illustrating greater stability in Table 10.

Additional examples follow.

Comparative Example 6

Illustrated in this example is a mixture of fenoxaprop p-ethyl, mefenpyr diethyl, pyrasulfotole, bromoxynil mixed esters and fillers which was prepared in similar manner as in Example 1 or Comparative Example 4, but without a buffer system of the invention (see Table 11).

TABLE 11

INGREDIENTS

Pyrasulfotole (99% pure), 3.188%
Bromoxynil mixed esters, 17.85%
Mefenpyr diethyl (94.8% pure), 2.915%
Fenoxyprop p-ethyl (94% pure), 7.810%
[1]Alkyl alcohol ethoxylate, 6%
Benzene sulfonic acid calcium Salt, 4%
Epoxidized soy oil, 2%
[2]Ethoxylated sulfate, 6%
Propylene carbonate, 15%
[3]Aromatic organic solvent, 34.24%
2-ethylhexanol, 1%

[1]Containing on the average an aliphatic chain of 11 to 15 carbons and ethoxylated to an average of 4 to 8 moles
[2]Ammonium salt of tristyrylphenol that includes 12 to 20 moles of ethylene oxide
[3]A150 commercially available from Exxon Corporation.

The mixture was tested for long-term storage stability by subjecting separate samples to different temperatures for eight weeks. The following test results were obtained and shown in Table 12.

TABLE 12

| name | Avg. Wt % Pyrasulfotole | Avg. Wt % Active ingredient Mefenpyr diethyl | Avg. Wt % Bromoxynil Mixed Esters | Avg. Wt % Fenoxaprop p-ethyl |
|---|---|---|---|---|
| 8 weeks @ 0° C. | 3.26 | 2.98 | 17.84 | 6.97 |
| 8 weeks @ room temp. | 3.01 | 3.00 | 18.89 | 6.15 |
| change from 0° C. | −7.67% | 0.67% | −1.40% | −11.76% |
| 8 weeks @ 40° C. | 2.81 | 3.01 | 17.50 | 2.34 |
| change from 0° C. | −13.8% | 1.01% | −1.91% | −66.43% |
| 8 weeks @ 50° C. change from 0° C. | | | | |

Example 7

In this example, an emulsifiable concentrate of fenoxaprop p-ethyl, mefenpyr diethyl, pyrasulfotole and bromoxynil mixed esters was prepared. Triethanolamine, a buffer that is capable of hydrogen bonding, was selected as the buffer. Dodecylbenzenesulfontate calcium, also known as DBSCa was also used to provide a calcium cation for the complex. The mixture of Table 13 was prepared by mixing the liquid ingredients, then the solid ingredients at 50° C.

TABLE 13

| INGREDIENTS |
| --- |
| Pyrasulfotole (99% pure), 3.260% |
| Bromoxynil mixed esters, 18.40% |
| Mefenpyr diethyl (94.8% pure), 2.980% |
| Fenoxyprop p-ethyl (94% pure), 8.00% |
| [1]Alkyl alcohol ethoxylate, 6% |
| Benzene sulfonic acid calcium Salt, 4% |
| Epoxidized soy oil, 2% |
| [2]Ethoxylated sulfate, 6% |
| Triethanolamine, 1% |
| Propylene carbonate, 15% |
| [3]Aromatic organic solvent, 33.30% |

[1]Containing on the average an aliphatic chain of 11 to 15 carbons and ethoxylated to an average of 4 to 8 moles
[2]Ammonium salt of tristyrylphenol that includes 12 to 20 moles of ethylene oxide
[3]A150 commercially available from Exxon Corporation.

The mixture was tested for long-term storage stability by subjecting separate samples to room temperatures for 1 year. The following test results were obtained and shown in Table 14.

TABLE 14

| Active ingredient name | Avg. Wt % Pyrasulfotole | Avg. Wt % Mefenpyr Diethyl | Avg. Wt % Bromoxynil Heptanoate Esters | Avg. Wt % Bromoxynil octanoate Esters | Avg. Wt % Fenoxaprop p-ethyl |
| --- | --- | --- | --- | --- | --- |
| Expected | 3.26 | | 12.86 | 13.49 | 8 |
| 1 year @ room temp | 3.14 | | 12.47 | 13.08 | 7.95 |
| Change from expected | −3.083% | | −3.03% | −3.083% | −0.625% |

Example 8

A mixture of fenoxaprop p-ethyl, mefenpyr diethyl, pyrasulfotole, bromoxynil mixed esters and fillers was prepared in similar manner as in Example 1 or Comparative Example 4, with a buffer system of the invention (see Table 15), but without DBSCa as in the prior example.

TABLE 15

| INGREDIENTS |
| --- |
| Pyrasulfotole (99% pure), 1.4% |
| Bromoxynil mixed esters, 12.86% |
| Mefenpyr diethyl (94.8% pure), 1.84% |
| Fenoxyprop p-ethyl (94% pure), 4.040% |
| [1]Alkyl alcohol ethoxylate, 20% |
| Epoxidized soy oil, 2% |
| Etho-propoxylated tristyrylphenol, 2% |
| Propylene carbonate, 15% |
| Triethanolamine 0.6% |
| [2]Aromatic organic solvent, 39.26% |
| 2-ethylhexanol, 1% |

[1]Containing on the average an aliphatic chain of 11 to 15 carbons and ethoxylated to an average of 4 to 8 moles
[2]A150 commercially available from Exxon Corporation.

The mixture was tested for long-term storage stability by subjecting separate samples to different temperatures for eight weeks. The following test results were obtained and shown in Table 16.

TABLE 16

| | Avg. Wt % | Avg. Wt % | Avg. Wt % | Avg. Wt % |
| --- | --- | --- | --- | --- |
| | Active ingredient name | | | |
| | Pyrasulfotole | Mefenpyr diethyl | Bromoxynil Mixed Esters | Fenoxaprop p-ethyl |
| 8 weeks @ 0° C. | 1.74 | 1.74 | 8.20 | 4.33 |
| 8 weeks @ room temp. change from 0° C. | | | | |
| 8 weeks @ 40° C. | 1.65 | 1.72 | 7.50 | 4.00 |
| change from 0° C. | −4.81% | −1.29% | −6.25% | −5.75% |
| 8 weeks @ 50° C. change from 0° C. | | | | |

As may be seen with Examples 7 and 8, stability is achieved, although results with the calcium cation were superior in that there was less pyrasulfotole degeneration in Table 16. The inventors postulate that even without the presence of the calcium cation, the triethanolamine may function in a protonated form possibly with hydrogen bonding, to form the a complex similar to that which forms when a calcium cation is present.

As may be seen by comparing the results of Examples 4, 5, 6, 7, and 8 surprisingly only the triethanolamine containing herbicidal composition provided the desired stability. And of course, Comparative Example 6 illustrates the poor results obtained when no buffer is used with the combination of fenoxaprop p-ethyl, pyrasulfotole, bromoxynil mixed ester and mefenpyr diethyl.

The inventors have found that in Examples 4, 5, 7 and 8, the amine-containing buffer, whether capable of complexing or not, operates to prevent an undesired acid-catalyzed hydrolysis of fenoxaprop p-ethyl, illustrated in FIG. 1. As shown in FIG. 1, pyrasulfotole contains an hydroxyl (OH) group which reacts with fenoxaprop p-ethyl to transfer a proton from pyrasulfotole to fenoxaprop p-ethyl, whereupon fenoxaprop p-ethyl is cleaved into 6-chlorobenzooxazole-2 (3H)-one and ethyl 2-(4-hydroxyphenoxy) propionate with the concurrent formation of a pyrasulfotole anion (having had its hydrogen donated to the cleavage of fenoxaprop p-ethyl). When bromoxynil mixed esters is not present, as in Comparative Examples 1 and 3, this acid catalyzed hydrolysis which causes the undesirable degradation of fenoxaprop p-ethyl is overcome by the presence of an amine-containing buffer, (whether or not it is capable of hydrogen bonding).

Where the amine-containing buffer is not capable of complexing (e.g. hydrogen bonding) (e.g. triethylamine) it operates to buffer the system which prevents the acid-catalyzed hydrolysis of fenoxaprop p-ethyl.

Where the amine-containing buffer is capable of forming a complex (optionally preferably also engaging in hydrogen bonding or otherwise forming a coordination complex) (e.g. triethanolamine), it may operate along the same pathway as the non-hydrogen bonding amine-containing buffer described immediately above, but it also forms a complex with the pyrasulfotole anion, as explained in more detail below. In the absence of unstable or relatively unstable ester containing moieties such as bromoxynil mixed esters, the pyrasulfotole anion not exposed to further degradation from a transesterification process described below, and thus both the complexing (e.g. hydrogen-bonding or otherwise forming a coordination complex) compounds (e.g. triethanolamine) and the non-hydrogen bonding or non-complexing compounds (e.g. triethylamine) operate in such a non-bromoxynil mixed esters containing system to stabilize the herbicidal composition with similar efficacy. Thus, whether capable of complexing or not, (e.g. whether triethanolamine or triethylamine) the amine-containing buffer helps prevent undesirable degradation of the herbicidal composition that does not contain unstable or relatively unstable esters such as that of bromoxynil esters.

While the presence of the amine-containing buffer whether complexing or not, operates to reduce the amount of acid-catalyzed hydrolysis and therefore leads to a more stable herbicidal composition, where a compound such as bromoxynil mixed esters is present, yet another undesirable reaction mechanism occurs which only the complexing-capable amine-containing buffer (e.g. triethanolamine) can prevent or reduce.

More particularly, when the herbicidal composition also contains bromoxynil esters, as in Examples 4, 5, 6, 7 and 8 an additional reaction mechanism occurs. Bromoxynil esters as used in herbicidal compositions of the present invention, are present as mixed esters of bromoxynil, which esters are unstable or at least relatively less stable. As illustrated in FIG. 1, the pyrasulfotole anion provides a reactive site where these ester portion of the bromoxynil mixed esters can react to produce an undesirable transesterification of the pyrasulfotole anion into the undesirable ester mixture illustrated in FIG. 1, where R can be CH2-(CH2)4-CH3 or CH2-(CH2)5-CH3.

The reason for the different results in Examples 4, 5, 6, 7 and 8 is that when the complexing-capable amine-containing buffer (e.g. triethanolamine) forms its complex with the pyrasulfotole anion, the pyrasulfotole anion/hydrogen-bonding amine complex operates to shield or otherwise protect the reactive site of the pyrasulfotole anion from reacting with the bromoxynil mixed esters, thus preventing the undesirable transesterification of the pyrasulfotole anion, resulting in the desired stability of the herbicidal composition.

The complex structure has been isolated by the inventors, and proven to be in one embodiment 2×pyrasulfotole+1×triethanolamine+1×cation such as Ca(+2). Referring now to In FIG. 2 there is shown a single crystal x-ray structure analysis of such a complex of the present invention. Fast atom bombardment mass spectroscopy analysis (FAB MS analysis) was used to provide the molecular weight of the complex as 911, and with an additional proton as 912 for M+H. The structure was further confirmed by F-19 nuclear magnetic resonance, and finally by forming an independent synthesis of the complex with a solid phase C-13 NMR and FAB MS analysis.

Figure 2:
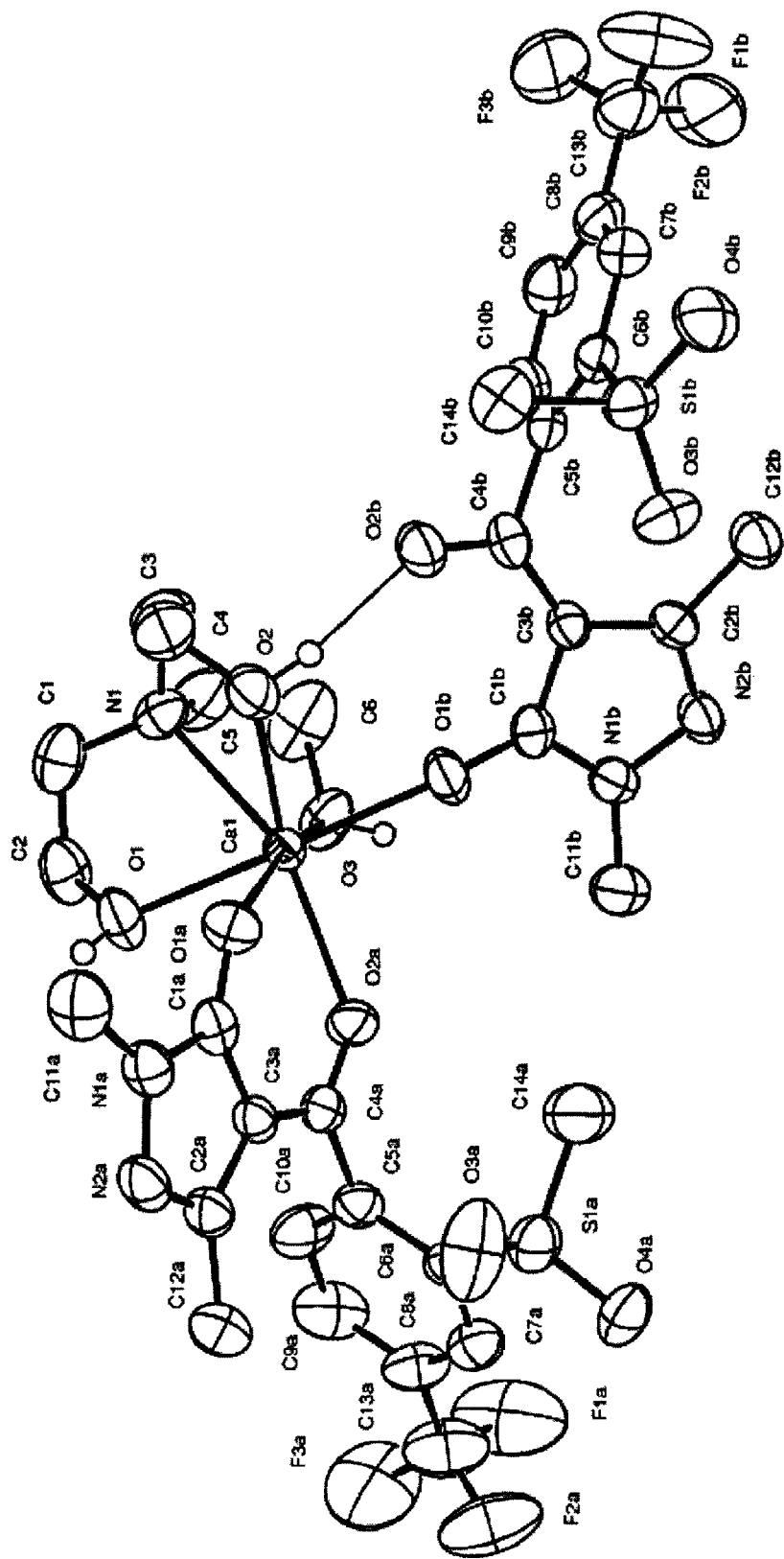
FIG. 2 is a single crystal x-ray structure analysis of the complex of the present invention.

With the present invention, as illustrated by way of non-limiting example by the x-ray structure of the embodiment shown in FIG. 2, two pyrasulfotole anions operate to complex with an amine-containing buffer, and optionally with a cation. Where the cation is present, it may be a metal or non-metal cation.

Speaking generally with regard to the novel complex of the present invention, where a metal cation is present, the term "complex" has the traditional meaning known by those skilled in the art to refer to metal coordination complexes (hereinafter "complex"). Where a non-metal cation is used, however, such non-metal cations do not form complexes as such but do form structures that are contemplated as within the scope of the invention. Unless otherwise clear from the context, as used herein, the term "complex" will refer to both metal and non-metal cations and to complexing-capable Lewis acids such as boron and aluminum containing Lewis acids. The coordination number of the novel complex of the present invention is dependent upon the cation selected and the ligands selected to form the complex as may be appreciated by those skilled in the art, but the coordination number may range from about 2 to 10 or more.

As an example of a non metallic cation, where the herbicidal composition includes triethanolamine, a first triethanolamine molecule in the composition may operate to form a part of the complex, while a second triethanolamine may contain a protonated nitrogen that functions as a cation.

The inventors postulate, but are not limited to the concept, that the amine-containing compound that is capable of complexing may additionally exhibit hydrogen bonding. The x-ray structure illustrated in FIG. 2 is consistent with hydrogen bonding.

With regard to metal cations, calcium is a preferred cation due to its fortunate presence in many herbicidal compositions from its use as a wetting agent, but the present invention is not limited to calcium cations.

Metal cations included within the scope of the present invention include earth metal ions, alkaline earth metal ions, transition metal ions or cations capable of forming complexes such as calcium, magnesium, lithium sodium, potassium, copper, silver, ferrous ion, ferric ion, aluminum, cobalt, nickel, titanium, chromium, manganese, barium, beryllium, boron and zinc, or combinations thereof. Other cation donating agents can include inorganic salts such as NaCl, $MgCl_2$, $CaCl_2$, or $CaSO_4$ or combinations thereof.

Non-metal cations included various ammonium ions known in the art including ammonium, protonated amines, quaternary ammonium and protonated primary amine, protonated secondary amine, protonated tertiary amine such as protonated triethanolamine and protonated triisopropoanolamine.

Where no metal cations are present, even the triethanolamine or other amine-containing compound can function as the cation if it is in protonated form.

As shown in FIG. 2, the calcium cation (Ca+2) is surrounded by two pyrasulfotole anions which have formed a complex with triethanolamine. Also as illustrated in FIG. 2, at least one of the hydroxyl groups of the three present with triethanolamine appears to offer its hydrogen atom consistent with hydrogen bonding with one of the oxygen atoms present in one of the pyrasulfotole anions, such as the carbonyl oxygen atom. The complex illustrated in FIG. 2 renders the pyrasulfotole incapable undergoing transesterification or less tendency to undergo transesterification with any of the bromoxynil mixed esters, thus preventing or reducing the tendency to undergo the unwanted transesterification-based degradation of the herbicidal composition.

Thus, in one embodiment, the complex of the present invention is composed of 2 mole equivalents of pyrasulfotole, 1 mole equivalent of a cation such as Ca(+2) and 1 mole equivalent of triethanolamine. The complex is an unsymmetrical complex molecule, indicating a hydrogen bonding between a C=O group of the pyrasulfotole and an OH group of the triethanolamine.

In an effort to confirm their analysis, the inventors synthesized the novel complex.

The novel complex can be synthesized by combining a keto-enol, a hydroxyalkyl and a metal ion provider in a pH range preferably from neutral to slightly basic in wide variety of solvents such as aprotic or protic solvents. In one embodiment, pyrasulfotole, triethanolamine and dodecylbenzenesulfontate calcium in a suitable stoichiometric amount, preferably in an excess of triethanolamine to ensure the slight basicity of the mixture. Other metal ion providers could include alkyl benzene sulfonate calcium such as octylbenzene sulfonate calcium or a long-chain only (no phenyl ring involved) sulfonate calcium.

A preferred pH range in synthesizing the complex is from about 4.5 to about 10, preferably from about 6.0 to about 8.0. The inventors have found that controlling the pH can be important because as the reaction approaches higher temperatures it was more likely to prevent stable formation of the complex if the reaction mixture was allowed to become too acidic at those higher temperatures.

The reaction can occur in the range of from about −20° C. to about 250° C., preferably about 0° C. to about 150° C., most preferably in the range of about 25° C. to about 120° C. Preferably, the combination is heated, with or without reflux and at atmospheric pressure or at a pressure or pressures above atmospheric pressure to reflux in a suitable solvent such as benzene, toluene, propylene carbonate, Aromatic 100, Aromatic 150 or Aromatic 200 or in mixtures thereof. The reaction time may be from minutes to several weeks, but a reflux in benzene for approximately 3 days or heated in propylene carbonate and benzene mixture at 60° C. for about 14 days may be used.

Alternatively, the complex may be synthesized using a strong base such as a hydride to form salts of pyrasolfotole in anhydrous solvents. For example, calcium hydroxide may be used as a base to form calcium salts of pyrasulfotole in aromatic solvents such as benzene, toluene, xylene, Aromatic 150, Aromatic 200, amides such as dimethylforamide (DMF), ethers such as tetrahydrofuran (THF), diethyl ether, or dimethoxyethane (DME). Upon formation of the salt of pyrasulfotole, the reaction is quenched with a suitable amount of triethanolamine.

In either of the above methods, the complex is preferably isolated by precipitation, filtered and washed with suitable solvent in suitable quantity. The solvent for example, may be acetone or methylene chloride. The complex formed may be in crystalline or non-crystalline form (e.g. an amorphous form), or combinations thereof, with the crystal form being preferred. Either way, the complex will precipitate from solution.

After precipitation, the precipitate whether in solid, powder, crystalline or non-crystalline form, or combinations thereof, is filtered and washed with acetone or methylene chloride as many times as needed, typically one or two times, to give a reasonably pure complex.

When the inventors synthesized the complex, upon analysis it was shown to be the same as that described above and illustrated in FIG. 2 using FAB MS, NMR solid C-13 NMR and liquid state (C-13, F-19 and H-1 NMR).

While other methods may be contemplated to synthesize the complex, the processes of the present invention have the advantage of providing a clean isolation of the complex and allow one-pot reactions preparation that has significant financial advantage.

Thus, the present inventors have isolated a novel chemical structure and a method for its synthesis which is known to provide stability to certain chemical compositions, and to certain herbicidal compositions in particular as set forth above. The complex of the present invention may be used to stabilize many chemical processes from degradation where a compound is present, such as pyrasulfotole, which is sensitive to unwanted transesterification reactions. Such compounds can be protected from such unwanted transesterification by formation of the novel complexes in accordance with the present invention.

In the broad sense, this invention is directed to employing a novel complex in a herbicidal formulation such as a suspension concentrate (SC), suspoemulsion (SE), emulsifiable concentrate (EC) or oil dispersible (OD) herbicidal formulation in which a base is used to stabilize the acid catalyzed hydrolysis and transesterification of one or more herbicides in the herbicidal composition. The bases used can be one or more organic bases, one or more inorganic bases or combinations thereof. As explained above, organic bases can include the amine compounds discussed in detail above. The inorganic bases can include cabonates, bicarbonates, phosphates, acetates and hydroxide salts of alkaline metals or alkaline earth metals such as sodium hydroxide, potassium hydroxide and calcium hydroxide or ammonium, such as ammonium hydroxide.

It should be noted that the inventors appreciate that mefenpyr also contains ester moieties capable of reacting in such a composition to facilitate undesirable transesterification of the pyrasulfotole anion. However, the inventors postulate that the stability of the mefenpyr ester is such that it does not contribute to the transesterification of the pyrasulfotole anion.

As may be appreciated by those skilled in the art, the novel herbicidal compositions of the present invention may be mixed with other ingredients such as but not limited to, fertilizers, fungicides, insecticides including miticides and nematicides, plant growth regulators, insect grown regulators and combinations thereof.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

The invention claimed is:

1. A complexing agent effective in stabilizing a herbicidal composition wherein said complexing agent is a reaction product of:
   a. a herbicidal compound capable of transesterification and subject to relatively rapid hydrolysis of the esters in the absence of a weak acid buffer system; and
   b. a weak acid buffer system,
   wherein the herbicidal compound is pyrasulfotole and the weak acid buffer system comprises triethanolamine.

2. The complexing agent of claim 1, further comprising a calcium cation.

3. A method for preventing an undesirable acid catalyzed hydrolysis of fenoxaprop ethyl and/or fenoxaprop p-ethyl and an undesirable transesterification of pyrasulfotole in a herbicidal composition which includes fenoxaprop p-ethyl, pyrasulfotole, and at least one component selected from the group consisting of bromoxynil, bromoxynil ester, bromoxynil mixed ester, and mefenpyr or mefenpyr diethyl comprising:

a. providing a herbicidal composition comprising fenoxaprop ethyl and/or fenoxaprop p-ethyl, pyrasulfotole, and at least one component selected from the group consisting of bromoxynil, bromoxynil ester, bromoxynil mixed ester, and mefenpyr;

b. adding triethanolamine to said herbicidal composition resulting in the formation of a complex with a;

whereupon said triethanolamine prevents an undesirable acid catalyzed hydrolysis of fenoxaprop ethyl and/or fenoxaprop p-ethyl and said complex prevents an undesirable transesterification of said pyrasulfotole.

4. A herbicidal composition comprising:
a. an acid-sensitive herbicide;
b. a weak acid herbicide;
c. an ester herbicide;
d. an optional safener; and
e. an optional cation donating agent;

wherein said herbicidal composition includes a complex, which complex prevents an acid catalyzed hydrolysis of said acid sensitive herbicide and prevents a transesterification of said weak acid herbicide, wherein said acid-sensitive herbicide is fenoxaprop p-ethyl, said weak acid herbicide is selected from the group consisting of pyrasulfotole, isoxaflutole, clethodim and sethoxydim, conjugates thereof and combinations thereof, said ester herbicide includes a bromoxynil ester, said optional safener is present and is mefenpyr diethyl, and said optional cation donating agent is present and is dodecylbenzenesulfonate calcium.

5. The composition of claim 4, further comprising an acidic herbicidally active ingredient.

6. A herbicidal composition comprising:
a. an acid-sensitive herbicide;
b. a weak acid herbicide;
c. an ester herbicide;
d. a buffer;
e. an optional safener; and
f. an optional cation donating agent;

wherein said herbicidal composition includes a complex, which complex prevents an acid catalyzed hydrolysis of said acid sensitive herbicide and prevents a transesterification of said weak acid herbicide, wherein:

a. said acid sensitive herbicide is present in said composition in a range of about 1 wt % to about 15 wt %;
b. said weak acid herbicide is present in said composition in a range of about 0.5 wt. % to 8 wt. %;
c. said ester herbicide is present in said composition in a range of about 1 wt. % to 30 wt. %;
d. said buffer is present in said composition in a range of about 0.1 wt. % to 10 wt. %;
e. said safener is present in said composition in a range of about 0.5 wt. % to 10 wt. %; and
f. said cation donating agent is present in said composition in a range of about 0.1 wt % to about 20 wt %, and wherein:
a. said acid-sensitive herbicide is fenoxaprop p-ethyl;
b. said weak acid herbicide is pyrasulfotole;
c. said ester herbicide includes one or more of bromoxynil and bromoxynil mixed esters;
d. said buffer includes triethanolamine;
e. said optional safener is present and is mefenpyr diethyl;
f. said optional cation donating agent is present and is dodecylbenzenesulfonate calcium.

7. The composition of claim 6, further comprising:
g. an acidic herbicidally active ingredient.

8. The composition of claim 7, wherein said acidic herbicidally active ingredient is selected from the group consisting of (4-chloro-2-methylphenoxy)-acetic acid, 2-(4-chloro-2-methylphenoxy)-propanoic acid, 4-(4-chloro-2-methylphenoxy)-butanoic acid, 2,4-D, dicamba and combinations thereof.

9. A method of controlling plants, including weeds, with a herbicidal composition comprising applying the composition of claim 6 to a plant, to seeds or other propagation material of a plant, to a locus of said plant, to a locus where there is no plant but where prevention of the growth of said plant is desired, and combinations thereof.

* * * * *